(12) United States Patent
Gueniche

(10) Patent No.: US 8,101,167 B2
(45) Date of Patent: Jan. 24, 2012

(54) CONDITIONED MEDIUM AND USES THEREOF

(75) Inventor: Audrey Gueniche, Rueil Malmaison (FR)

(73) Assignee: L'Oreal, Paris (FR)

( * ) Notice: Subject to any disclaimer, the term of this patent is extended or adjusted under 35 U.S.C. 154(b) by 499 days.

(21) Appl. No.: 12/037,198

(22) Filed: Feb. 26, 2008

(65) Prior Publication Data

US 2008/0206171 A1    Aug. 28, 2008

Related U.S. Application Data

(60) Provisional application No. 60/907,341, filed on Mar. 29, 2007.

(30) Foreign Application Priority Data

Feb. 26, 2007  (FR) ..................................... 07 53496

(51) Int. Cl.
*A01N 63/00*    (2006.01)

(52) U.S. Cl. ........ 424/93.1; 435/41; 435/70.3; 435/325; 435/386

(58) Field of Classification Search ......................... None
See application file for complete search history.

(56) References Cited

U.S. PATENT DOCUMENTS

| | | | |
|---|---|---|---|
| 7,547,527 B2 * | 6/2009 | Baur et al. ....................... | 435/41 |
| 2004/0063722 A1 * | 4/2004 | Whitefield et al. ...... | 514/254.07 |
| 2006/0171936 A1 * | 8/2006 | Gueniche et al. .......... | 424/93.45 |

FOREIGN PATENT DOCUMENTS

| | | |
|---|---|---|
| WO | WO 02/28402 | 4/2002 |
| WO | WO 02/098365 | 12/2002 |
| WO | WO 2005/077389 | 8/2005 |
| WO | WO 2006/037922 | 4/2006 |

OTHER PUBLICATIONS

Gueniche et al., Eur. J Dermatol., 2006, vol. 16, No. 4, p. 380-384.*
Cross et al., International Immunopharmacology, 2001, vol. 1, p. 891-901.*
Blum et al., The influence of intestinal microflora on mucosal and systemic immune responses, in "Novel Frontiers in the Production of Compounds for Biomedical Use", 2001, Edited by Broekhoven et al., pp. 429, 434, 435, 437 and 438.*
Satsu Hideo et al. "Food Factors that Regulate Intestinal Inflammation: Evaluation of the Factors by Using a Coculture System," Animal Cell Technology: Basic and Applied Aspects, 2006, pp. 29-37; XP009091859.
U.S. Appl. No. 12/037,179, filed Feb. 26, 2008, Gueniche.

* cited by examiner

*Primary Examiner* — Kade Ariani
(74) *Attorney, Agent, or Firm* — Oblon, Spivak, McClelland, Maier & Neustadt, L.L.P.

(57) ABSTRACT

The invention relates to compositions containing an agent that has an irritant side effect and a conditioned cell culture medium and/or of an extract thereof, for use, e.g., in the treatment of signs of inflammation and/or of immune disorders, the medium being obtainable by contact with at least one culture of digestive tract cells and at least one probiotic microorganisms. Methods of use.

8 Claims, No Drawings

CONDITIONED MEDIUM AND USES THEREOF

REFERENCE TO PRIOR APPLICATIONS

This application claims priority to U.S. provisional application 60/907,341 filed Mar. 29, 2007, and to French patent application 0753496 filed Feb. 26, 2007, both incorporated herein by reference.

FIELD OF THE INVENTION

The present invention relates to conditioned culture media, extracts thereof, and the compositions containing them and to the uses thereof, in particular in the cosmetics or dermatological field. It also relates to the treatment and prevention of the signs of irritation of inflammation or immunological disorders with such conditioned media, extracts thereof, and the compositions containing them. The invention also relates to a composition comprising the combination of at least one cosmetic or pharmaceutical compound capable of causing an irritation of the skin and of at least one conditioned culture medium or of an extract thereof according to the invention.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

Human skin comprises two compartments, namely a superficial compartment, the epidermis, and a deep compartment, the dermis.

The epidermis is composed mainly of three types of cells, which are the keratinocytes (predominant), the melanocytes and the Langerhans cells. Each of these cell types contributes by means of its intrinsic functions to the essential role played in the body by the skin, in particular the role of protecting the body against outside attacks. The dermis provides the epidermis with a solid support. It is also its nourishing element. It is mainly constituted of fibroblasts and an extracellular matrix, itself composed mainly of collagen, elastin and a ground substance. Leukocytes, mast cells and tissue macrophages are also found therein. Finally, blood vessels and nerve fibres traverse the dermis.

The skin constitutes a barrier against outside attacks, in particular: chemical, mechanical and infectious attacks, and in this respect, a certain number of defense reactions against environmental factors (climate, ultraviolet rays, tobacco, pollution, infections, etc.) and/or xenobiotic factors (such as, for example, certain medicaments) occur therein.

It is therefore essential to preserve or re-establish its integrity and the equilibrium of its various functions, in particular an equilibrium between the cell renewal and differentiation processes, or an optimum degree of moisturization.

Skin irritation is conventionally defined as a reversible and non-immunological local inflammatory reaction, characterized by an oedema and an erythema induced after simple or repeated contact between a chemical substance and the skin.

Acute irritant contact dermatitis (ICD) is mainly characterized by an inflammation, whereas chronic ICD is characterized by keratinocyte hyperproliferation and transient hyperkeratosis. ICD is a multifactoral disease, the triggering of which depends on both intrinsic and extrinsic factors. Age, genetic background and sex all constitute factors which can influence the development of this pathology. Furthermore, the effects of irritants are directly linked to their chemical properties and to the concentrations applied, which influence cutaneous absorption.

Skin irritation is a very important phenomenon since it represents approximately between 60% and 80% of clinical cases of contact dermatitis. The majority of the other cases represent allergic contact dermatitis.

Substances belonging to various families of very different chemical products, such as keratin solvents, dehydrating agents or oxidizing or reducing agents may be considered to be irritants. Because of this heterogeneity, it is very difficult to propose a method for discriminating an irritant product using its chemical structure as a basis. Various irritants may induce various types of inflammations. In addition to their corrosive effects, which induce the release of preformed inflammatory mediators, chemical products may impair the cellular functions or induce the activation of the skin cells of innate immunity. This results in the release of numerous inflammation-specific compounds such as cytokines, chemokines, complement compounds and vasodilatory compounds such as histamine or the metabolites of the arachidonic acid pathway which modulate skin inflammation and cell recruitment.

Penetration of the skin by chemical compounds is a major parameter in establishing the physiopathology of ICD (Norlen L et al., J. Invest Dermatol 117: 823-829, 2001, Mizutani H et al., J. Clin Invest 87: 1066-1071, 1991). Said penetration is linked to the degree of permeability of the skin (which is linked to its physiological condition) and to the physicochemical properties of the compounds whose entry it is supposed to restrict (molecular weight, polarity, ionization stage) and the nature of the environment (excipient, carrier) through which these substances are brought into contact with the skin.

This important step corresponds to the release, from the outside environment or the carrier, of the molecule which will diffuse, and therefore to it becoming available to the body.

When an irritant comes into contact with the skin, the keratinocytes are the first cells to be activated by the chemical compound. Most of the studies on ICD have thus focused on this cell type and a large amount of data is now known about their participation in the physiopathology of ICD. Keratinocytes play an important role in the initialization of the cutaneous inflammatory reaction through the release of numerous mediators and of cytokines responsible for an entire cascade of inflammation resulting in the clinical signs of ICD. Among these, IL-1α and arachidonic acid derivatives are of particular importance in the development of the inflammation.

The release of IL-1α induces, via the activation of the NF-kB transcription factor, the transcription of genes involved in inflammation, such as the cytokines IL-1β, IL-6, GM-CSF, TNFα, chemokines, including IL-8, MCP-1, MIP-1α and eotaxin, and also the expression of adhesion molecules such as E-selectin or ICAM-1 and VCAM-1 (Gordon J R, Nature 19: 346 (6281): 274-276).

The signalling cascade generated from the activation of keratinocytes begins from the release of prestored key mediators. In fact, resting keratinocytes contain large amounts of preformed and biologically active IL-1α (Marks F et al., Toxicol Lett 96: 111-118, 1998), and also of arachidonic acid (Murphy J E et al., J Invest Dermatol 114: 602-608, 2000). Because these two compounds are constitutively produced by keratinocytes, and remain stored in the cell, the epidermis may be considered to be a major reservoir of highly inflammatory mediators. An impairment of the keratinocytes due to the corrosive effect of a chemical compound, a burn or UV exposure induces the release of IL-1α and of arachidonic acid, which become the body's first defense events. IL-1α not only has an autocrine role, but has been described as inducing the transcription of more than 90 different genes on various skin cell types, such as keratinocytes, endothelial cells or fibroblasts, through the activation of the NF-kB transcription factor pathway (Gordon J R, Nature 19: 346 (6281): 274-276).

Arachidonic acid is, for its part, rapidly metabolized to many highly active compounds, eicosanoids such as prostaglandins, thromboxane and leukotrienes acting as local mediators with a short lifetime, involved in the control of proliferation, differentiation, apoptosis, or else the formation of oedema or leukocyte activation (Murphy J E et al., J Invest Dermatol 114: 602-608, 2000).

Thus, IL-1α and arachidonic acid could be considered to be the key mediators for triggering the irritation in response to a chemical stress (Murphy J E et al., J Invest Dermatol 114: 602-608, 2000).

Among all the inflammatory mediators, besides IL-1s and arachidonic acid, only TNF-α can activate a sufficient number of mechanisms to independently generate a skin inflammation. This major cytokine of skin inflammation is already prestored in the dermal mast cells (Larrick J W et al., J Leukoc Biol 45: 429-433, 1989) but is also produced by the keratinocytes and the Langerhans cells after stimulation (Groves R W, et al., J Invest Dermatol 98: 384-387, 1992). One of the mechanisms through which TNF-α has most influence on the inflammatory reaction is the induction of adhesion molecules in synergy with IL-1. Adhesion molecules play an essential role in the circulation and penetration of leukocytes (in particular neutrophils) from the peripheral blood vessels to the dermis and the epidermis (Holliday M R et al., Am J Contact Dermat 8: 158-164, 1997).

A large amount of chemical products can induce a skin irritation; however, they differ in terms of their ability to generate pro-inflammatory cytokines and a skin inflammation is not systematically dependent on the production of TNF-α.

It is important to also note that the production of IL-12 and of IL-18 by the activated macrophages at the site of the inflammation plays an important role as a local amplification loop. This is because these cytokines stimulate the production of IFN-γ by neighbouring T lymphocytes, which is in turn a powerful coactivation factor for the macrophages and the keratinocytes.

Furthermore, chemokine secretion by the vascular cells and the keratinocytes occurs. The chemokines of the CC subgroup (so-named since the first cysteines are contiguous), the prototype of which is IL-8, are chemotactic with respect to polymorphonuclear cells and certain lymphocytes. The chemokines of the CXC group (so-named because an amino acid is integrated between the first two cysteines), the prototype of which is MCP-1 (monocyte chemoattractant protein 1), are chemotactic with respect to monocytes/macrophages and certain lymphocytes. These two types of chemokines released at the inflammation site explain the polymorphic cellular infiltrate found in an inflamed tissue.

IL-6 is also a cytokine secreted by keratinocytes, macrophages and vascular cells activated during an inflammation. This important cytokine is involved in numerous systems, such as immune response, haematopoiesis, osteoblast proliferation, etc. In skin irritations, IL-6 is produced locally and may reach the general circulation and trigger regional and general effects.

In parallel to the cytokines and chemokines and also the arachidonic acid metabolites, another major inflammation mediator is oxidative stress.

Certain chemical irritants are known to generate free radicals and ROSs (reactive oxygen species) capable of inducing lipid peroxidation or DNA alteration. The hypothesis that oxidative stress plays a role in the phenomena of irritation induced by a chemical compound is supported by the fact that ROS inhibitors/scavengers inhibit skin inflammation (Zhang L et al., J Invest Dermatol 115: 168-176, 2000).

Although Langerhans cells (LC) play a fundamental role in the induction of an antigen-specific response, they do not appear to have a major role in the physiopathology of ICD. Many studies have described changes in morphology or in density of LCs after epicutaneous application of irritants (Mikulowska A et al., Contact Dermatitis 34: 397-401, 1996; Kimber I et al., J Invest Dermatol 99: 48S-50S, 1992). However, these results could rather represent a non-specific response to the inflammatory reaction generated. It is now obvious that the IL-1α and the TNF-α produced during ICD have the ability to cause LCs to migrate in a dose-dependent manner. It may thus be that local concentrations of IL-1α and of TNF-α induced by irritants can generate a variable migration of LCs (Kimber I et al., J Invest Dermatol 99: 48S-50S, 1992).

Among the various populations of the cutaneous innate immune system, the mast cell is a major cell in the development of ICD. Mast cells are present in the dermis close to the blood vessels and are the only cells to contain prestored and biologically active TNF-α (Larrick J W et al., J Leukoc Biol 45: 429-433, 1989).

As opposed to these pro-inflammatory cytokines, there exist anti-inflammatory cytokines such as TGF-β and IL-10, and also shock proteins known to modulate any "danger" signal (i.e.: BiP (grp78) and HSP27) (Panayi G et al., Cur Opinion Immunol 16: 531-534, 2004).

It is therefore desirable to find novel ways for strengthening the skin's resistance to these deleterious mechanisms, and therefore for avoiding, treating or preventing inflammation and immunological disorders.

Application WO 02/098365 (Advanced Tissue Science) proposes the use of conditioned culture media for cosmetic or pharmaceutical applications. The conditioned media are obtained by culturing human skin cells, in particular fibroblasts or keratinocytes. These cells are genetically modified to increase their production of growth factors or of antioxidants in the medium, which generally contains a soluble collagen.

US 2005/0249691 describes cosmetic or dermatological compositions comprising a culture medium for cells of the skin or the horny layers, in combination with a gelled matrix; the compositions necessarily contain collagen, chitosans and glycosaminoglycans.

US 2006/0182701 also describes cosmetic or dermatological compositions comprising a culture medium for skin cells. It aims to provide the skin cells, to which the compositions are applied, with a medium which will allow them to develop in a similar manner to that which is obtained in vitro.

SUMMARY OF THE INVENTION

Unexpectedly, it has now been found, in the context of the present invention, that a culture medium conditioned by cells completely different from skin cells can be used to promote good condition of the skin or of its appendages and to combat inflammation and/or irritation and/or immunological disorders.

For this reason, a subject of the present invention is the use of at least one conditioned cell culture medium or of an extract thereof, for the preparation of a composition for use in the treatment of the signs of inflammation and/or of immune disorders, and such use thereof, said medium being able to be obtained by contact with at least one culture of digestive tract cells and at least probiotic microorganisms, also said medium being able to be obtained by contact with at least one culture of digestive tract cells and at least one probiotic microorganism.

Advantageously, the cell culture medium, also called conditioned medium according to the present invention, can be obtained by contact with peripheral blood cells, or cells derived from peripheral blood cells. Such cells are in particular leukocytes, but can also be selected from immortalized cell lines, derived from blood cell lines, for instance from monocytes; non limiting example of such cells are those sold by LGC Promochem under the following designations:
SC (ATCC: CRL-9855)
AML-193 (ATCC: CRL-9589)
THP-1 (ATCC: TIB-202). Mixtures may be used.
These peripheral blood cells or derivatives thereof, such as leukocytes may, for example, be in culture in the medium with the digestive tract cells.

Preferably, these leukocytes comprise predominantly lymphocytes, but may also comprise other peripheral blood cells such as monocytes, which are brought into contact with the medium. Mixtures may be used.

According to one of the advantageous embodiments of the invention, the culture of digestive track cells is a three-dimensional culture.

The digestive tract cells used for the implementation of the invention may be derived from various parts of the digestive tract, such as the esophagus, the stomach or the intestine. Advantageously, cells derived from the intestinal epithelium are used; such intestinal epithelial cells are known to those skilled in the art. By way of non-limiting example, mention may be made of the human cells of intestinal origin known as Caco2, HT29 or T84. Mixtures may be used.

The corresponding strains are deposited in the culture collections of the ATCC with the following Nos.:
Caco 2: ATCC No. HTB-37
HT29: ATCC No. HTB-38
T84: ATCC No. CCL-248
Mixtures may be used.

For the purpose of the present invention, the term "probiotic microorganism" is intended to mean a living microorganism which, when it is consumed in adequate amount, has a positive effect on the health of its host, "joint FAO/WHO Expert Consultation on Evaluation of Health and Nutritional Properties of Probiotic in Food Including Powder Milk with Live Lactic Acid Bacteria, 6 Oct. 2001", and which can in particular improve the intestinal microbial balance.

The probiotic microorganism may be introduced into the cell culture medium in the form of a suspension of live cells, the concentration of which will be adjusted by those skilled in the art according to the amount of the other constituents of the mixture. By way of indication, it is possible to use an inoculum comprising approximately $10^4$ to $10^9$ cfu/ml (cfu signifying "colony forming unit", i.e. "unit capable of forming a colony"), preferably at least $10^5$ cfu/ml. The probiotic inoculum may conventionally be at a concentration of approximately $10^6$ to $10^7$ cfu. Mixtures may be used.

The microorganisms suitable for the invention may be chosen in particular from ascomycetes such as *Saccharomyces, Yarrowia, Kluyveromyces, Torulaspora, Schizosaccharomyces pombe, Debaromyces, Candida, Pichia, Aspergillus* and *Penicillium*, and bacteria of the genus *Bifidobacterium, Bacteroides, Fusobacterium, Melissococcus, Propionibacterium, Enterococcus, Lactococcus, Staphylococcus, Peptostrepococcus, Bacillus, Pediococcus, Micrococcus, Leuconostoc, Weissella, Aerococcus, Oenococcus* or *Lactobacillus*, and mixtures thereof.

As ascomycetes that are most particularly suitable for the present invention, mention may in particular be made of *Yarrowia lipolitica* and *Kluyveromyces lactis*, along with *Torulaspora, Schizosaccharomyces pombe, Candida* and *Pichia*, or alternatively yeasts such as *Saccharomyces cerevisiae* or *boulardii*. Mixtures may be used As regards the probiotic microorganisms, it is the following bacterial and yeast genera that are generally used:
  lactic acid bacteria: which produce lactic acid by fermentation of sugar. They are divided up into two groups according to their morphologies:
    *Lactobacillus* species: *Lactobacillus acidophilus* (LC1, NCFB 1748); *amylovorus, casei* (Shirota), *rhamnosus* (strain GG), *brevis, crispatus, delbrueckii* (subsp *bulgaricus, lactis*), *fermentum, helveticus, gallinarum, gasseri johnsonii, paracasei, plantarum, reuteri, rhamnosus, salivarius*), *alimentarius, curvatus, casei* subsp. *casei, sake;*
    Gocci: *Enterococcus* (*faecalis, faecium*), *Lactococcus lactis* (subspp *lactis* or *cremoris*), *Leuconstoc mesenteroides* subsp *dextranicum*, *Pediococcus acidilactici, Sporolactobacillus inulinus, Streptococcus salvarius* subsp. *Thermophilus, Streptococcus thermophilus, Staphylococcus carnosus, Staphylococcus xylosus;*
  bifidobacteria or *Bifidobacterium* species: *Bifidobacterium adolescentis, animalis, bifidum, breve, lactis, longum, infantis, pseudocatenulatum;*
  the other sporulated bacteria: *Bacillus* (*cereus var toyo* or *subtilis*), *Bacillus coagulans, Bacillus licheniformis, Escherichia coli* strain *nissle, Propionibacterium freudenreichii*.
Mixtures may be used.

Specific examples of probiotic microorganisms are *Bifidobacterium adolescentis, Bifidobacterium animalis, Bifidobacterium bifidum, Bifidobacterium breve, Bifidobacterium lactis, Bifidobacterium longum, Bifidobacterium infantis, Bifidobacterium pseudocatenulatum, Lactobacillus acidophilus* (LC1, NCFB 1748); *Lactobacillus amylovorus, Lactobacillus casei* (Shirota), *Lactobacillus rhamnosus* (strain GG), *Lactobacillus brevis, Lactobacillus crispatus, Lactobacillus delbrueckii* (subsp *bulgaricus, lactis*), *Lactobacillus fermentum, Lactobacillus helveticus, Lactobacillus gallinarum, Lactobacillus gasseri, Lactobacillus johnsonii, Lactobacillus paracasei, Lactobacillus plantarum, Lactobacillus reuteri, Lactobacillus rhamnosus, Lactobacillus salivarius, Lactobacillus alimentarius, Lactobacillus curvatus, Lactobacillus casei* subsp. *casei, Lactobacillus sake Lactococcus lactis, Enterococcus* (*faecalis, faecium*), *Lactococcus lactis* (subspp *lactis* or *cremoris*), *Leuconstoc mesenteroides* subsp *dextranicum, Pediococcus acidilactici, Sporolactobacillus inulinus, Streptococcus salvarius* subsp. *Thermophilus, Streptococcus thermophilus, Staphylococcus carnosus, Staphylococcus xylosus, Saccharomyces* (*cerevisiae* or else *boulardii*), *Bacillus* (*cereus var toyo* or *subtilis*),

*Bacillus coagulans, Bacillus licheniformis, Escherichia coli* strain *nissle* and *Propionibacterium freudenreichii*, and mixtures thereof.

Advantageously, at least one probiotic microorganism is chosen from lactic acid bacteria, bifidobacteria and *Saccharomyces* yeasts.

More particularly, they are probiotic microorganisms derived from the lactic acid bacteria group, such as especially *Lactobacillus* and/or *Bifidobacterium*, in particular *Lactobacillus*. By way of illustration of these lactic acid bacteria, mention may more particularly be made of *Lactobacillus johnsonii, Lactobacillus reuteri, Lactobacillus rhamnosus, Lactobacillus paracasei, Lactobacillus casei* or *Bifidobacterium bifidum, Bifidobacterium breve, Bifidobacterium longum, Bifidobacterium animalis, Bifidobacterium lactis, Bifidobacterium infantis, Bifidobacterium adolescentis* or *Bifidobacterium pseudocatenulatum*, and mixtures thereof.

The species that are most particularly suitable are *Lactobacillus johnsonii, Lactobacillus paracasei, Bifidobacterium adolescentis, Bifidobacterium longum* and *Bifidobacterium lactis* NCC 2818 (also denoted Bb12 ATCC 27536); mention may in particular be made of the following strains, deposited according to the treaty of Budapest with the culture collection of the Institut Pasteur (28 rue du Docteur Roux, F-75024 Paris cedex 15) of 30, Jun. 1992, 12, Jan. 1999, 15, Apr. 1999, 15, Apr. 1999 and 7, Jun. 2005: *Lactobacillus johnsonii* (CNCM I-1225), *Lactobacillus paracasei* (CNCM I-2116), *Bifidobacterium adolescentis* (CNCM I-2168) and *Bifidobacterium longum* (CNCM I-2170) and *Bifidobacterium lactis* (CNCM I-3446), and the genus *Bifidobacterium longum* (BB536). The *Bifidobacterium lactis* CNCM I-3446 strain can be obtained from Hansen (Chr. Hansen A/S, 10-12 Boege Alle, P.O. Box 407, DK-2970 Hoersholm, Denmark). Mixtures may be used.

The cell culture medium with which the cells are brought into contact will be any nutritive medium suitable for the survival and/or the culture of the various cell types used. It generally contains a source of carbon and of nitrogen, minerals, vitamins and/or trace elements, for instance amino acids, sugars, proteins and fatty acids.

The cells may be cultured outside their tissue of origin. For this they should be cultured in an environment close to their natural condition in the tissue. These cultures require essential factors in their culture medium. This environment should have a defined composition composed of minerals and of biomaterials, known as culture medium. These culture media are in general provided by specialist suppliers and have specific characteristics according to the cell types. The culture media generally also contain water, a source of carbon and of nitrogen, phosphates and sulphates, minerals, growth factors and vitamins in suitable amount.

The cells cultured in this type of medium often require the addition of serum. This serum has a complex composition and provides the cells at least with hormones, adhesion factors and amino acids. This serum may, for example, be entirely or partly replaced with the addition of the conditioned media of the invention. In fact, the conditioned media may also be added, in addition, to the culture medium, as enrichment.

Those skilled in the art will readily determine the suitable media in view of this disclosure. In a non-limiting manner, mention may be made of RPMI 1640 medium, Dulbecco's Modified Eagle's Medium (DMEM), Minimum Essential Medium (MEM), M199, RPMI 1640 or Iscove's Modified Dulbecco's Medium (EDMEM), Ham's F-12, Ham's F-10, NCTC 109 and NCTC 135. Mixtures may be used.

These media may be supplemented with any additive normally used in cell culture, such as, for example, and in a non-limiting manner, phospholipid precursors, nonessential amino acids, nucleic acids, vitamins, antibiotics, enzymatic cofactors, mineral salts, insulin, transferrin, triiodothyronine, ethanolamine, O-phosphorylethanolamine or growth factors such as nerve growth factor or neurotrophin-3.

The concentrations of the various additives normally used for supplementing the cell culture media may be determined and adjusted by those skilled in the art, in particular according to the type of cells to be cultured, in view of this disclosure.

Other media are described in Ham and McKeehani, "*Methods in Enzymology*", 58:44-93, 1979, or else in Bottenstein et al., "*Methods in Enzymology*", 58:94-109, 1979, the content of which is incorporated herein by way of reference.

Moreover, it is also possible to use mixtures of various media, in particular of the above-mentioned media, such as for example a mixture of DMEM/HAM F12.

These media may be supplemented with specific growth factors, or for example with serum, but the latter component may also be absent.

According to one embodiment, no collagen is added to the culture medium.

This culture medium may be liquid, semi-liquid, gelled or solid, preferably at least partially liquid.

The expression "extract of the conditioned cell culture medium" is intended to mean in particular any fraction or subcompound of these conditioned media obtained by dialysis, fractionation, phase separation, filtration chromatography, affinity chromatography, precipitation, concentration, lyophilization, etc.

The conditioned media may be generated from media which may be devoid of serum and of animal product. This conditioned medium is preferably obtained after stimulation of the digestive tract cells in the presence of human leukocytes, with probiotics and in particular probiotics of the *lactobacillus* or *bifidobacterium* species.

Advantageously, the culture medium (or extracts thereof) used in the compositions of the invention is a stabilized medium, i.e. it has been subjected to a manipulation intended to preserve it in the state in which it existed at a selected given instant, generally at the end of its preparation process, while at the same time having conserved its intrinsic properties. In particular, this manipulation is intended to render said medium sterile, i.e. incapable of allowing the growth of microorganisms, while at the same time preserving the biological properties that it possesses. The stabilization of the culture medium may be obtained by any technique known to those skilled in the art, such as, for example, sterilizing filtration, autoclaving, ultra-high temperature (UHT technique), high-pressure sterilization, $\gamma$-radiation or freezing. The conditioned culture media according to the invention generally contain IL-10, which was not present among the different constituents of the starting medium. The amount of IL-10 may vary, according to the conditions of preparation of the conditioned culture medium but will correspond generally to a concentration greater or equal to 20 pg/ml of the medium recovered after contact with the different cellular types.

The conditioned culture medium according to the invention, the extracts thereof or the compositions containing it are particularly useful for preventing, reducing or treating the signs of skin irritation.

Skin reactions, in particular skin irritation, may be induced by an exogeneous stress of chemical origin, for example xenobiotics, antigens, allergens, chemical products, compounds capable of causing skin irritation, or a peel, of environmental origin (temperature, climate, UV radiation, atmospheric pollution, in particular heavy metals, ozone, cigarette smoke, etc.) or else of mechanical origin (friction, shaving), and any stress of endogenous origin such as disorders involving an inflammatory and/or hormonal mechanism affecting the skin, a mucous membrane, the scalp and/or the hair.

The physiological endogenous stress may, for example, be associated with the abnormal production of pro-inflammatory mediators (neuromediators, cytokines, chemokines) or with an androgenetic alopecia.

A subject of the invention is in particular the use of at least one conditioned culture medium or of at least one extract as defined above, in or for the preparation of a composition for use in treating the signs of irritation of the skin and/or of the scalp.

Thus, the invention relates to the non-therapeutic use of at least one conditioned medium or extracts thereof, as a calmative.

A subject of the invention is also said non-therapeutic use of at least one conditioned medium or extracts thereof according to the present invention, for preventing and/or treating skin reactions chosen from redness, itching, heat sensations, burning sensations, stinging and tautness.

A subject of the invention is also said use according to the present invention, wherein said conditioned medium or extracts thereof is for use in preventing and/or reducing said skin reaction induced by at least one condition chosen from the action of xenobiotics, of antigens, of allergens, of chemical products, of compounds capable of causing a skin irritation, or of a peel, or the action of the temperature, of the climate, of UV radiation or of atmospheric pollution, or alternatively by friction, the abnormal production of pro-inflammatory mediators and androgenetic alopecia.

The conditioned medium or extracts thereof may in particular be for use in preventing and/or reducing the irritant effect of a cosmetic or dermatological composition containing one or more compounds capable of causing an irritation.

A subject of the invention is also a process for claming the skin and preventing and/or treating skin reactions chosen from redness, itching, heat sensations, burning sensations, stinging and tautness, wherein at least one cell culture medium or at least one culture medium extract or a composition containing the same, is applied to the skin or the scalp, said medium being able to be obtained by contact with at least one culture of digestive tract cells and at least probiotic microorganisms, as defined in the above text.

A subject of the invention is also the use of at least one conditioned medium or extracts thereof, for the preparation of a compound for use in preventing and/or treating skin disorders related to a skin irritation, for example encountered in individuals with irritable and/or allergic skins and/or mucous membranes and/or scalps.

A subject of the invention is more particularly said use for the preparation of a composition for use in preventing and/or treating skin irritation, wherein the skin irritation is induced by at least one condition chosen from the action of xenobiotics, of antigens, of allergens, of chemical products, of compounds capable of causing a skin irritation, or of a peel, or the action of the temperature, of the climate, of UV radiation or of atmospheric pollution, or alternatively by friction, the abnormal production of pro-inflammatory mediators and androgenetic alopecia.

A subject of the invention is also the use of at least one conditioned medium or extracts thereof, for the preparation of a composition for use in preventing and/or treating skin disorders related to a skin reaction, for example of inflammatory or immunoallergic type.

Thus, the conditioned media or the compositions according to the invention are more particularly of use for combating skin disorders chosen from dry patches, oedema and/or spots, inflammatory erythema; pruritus; psoriasis, cutaneous atopy, atopic dermatitis; urticaria; contact dermatitis; eczema; seborrheic dermatitis; acne; inflammatory hyperpigmentations; immune dermatoses; bullous immune diseases; scleroderma; actinic elastosis; pelade or *alopecia greata*; vitiligo; systemic lupus erythematosus; *pemphigus vulgaris*; dystrophic epidermolysis bullosa and canities of autoimmune origin.

In fact, it is known that certain skin disorders are related to a skin reaction of inflammatory or immunoallergic type, among which are inflammatory erythema, psoriasis, cutaneous atopy, atopic dermatitis, allergic reactions of immediate hypersensitivity type, such as urticaria, allergic reactions of delayed hypersensitivity type, such as contact dermatitis, eczema; seborrheic dermatitis, acne, inflammatory hyperpigmentations, immune dermatoses, actinic elastosis, pelade or *alopecia greata*; vitiligo; systemic lupus erythematosis; *pemphigus vulgaris*; dystrophic epidermolysis bullosa and canities of autoimmune origin.

Furthermore, in terms of the skin, UV exposures generate strictly inflammatory reactions and have irritant effects, which may lead to the development of an erythema, an oedema and/or hyperkeratosis. These inflammatory and/or irritation reactions are associated with a stimulation of specific players of the immune system.

According to one of the embodiments of the invention, the conditioned medium or the compositions according to the invention are for use in protecting the skin cells against damage caused by UV radiation.

The conditioned medium or the compositions according to the invention are advantageously for use in protecting the cells, in particular the skin cells, against damage to their DNA.

The compositions are in particular for use in:
1) repairing altered DNA and thus reducing the risk of cancer (for example, induced in the skin following environment-related stress). These substances could in particular influence the main mechanism of repair of the genetic material in mammals, nucleoside-excision repair;
2) inhibiting caspases in the case of atopic dermatitis or of contact allergy, inhibiting the activated T cells infiltrating the skin of affected individuals which induce apoptosis of the neighbouring keratinocytes. Thus, the number of apoptotic keratinocytes could be reduced, and therefore the loss of intercellular cohesion (acantholysis) and, consequently, vesicle formation.

Moreover, the use of certain topical compounds may, under specific circumstances such as reactive skin, skin affected by rosacea, high concentrations of said compounds, etc., lead to the appearance of skin reactions, are used in cosmetic or dermatological compositions, of course for other effects.

Thus, compositions containing, for example, keratolytic and/or desquamating active agents are used for combating ageing, and in particular exfoliating active agents and/or active agents for promoting cell renewal, such as α-hydroxy acids (in particular lactic acid, glycolic acid, citric acid), β-hydroxy acids (in particular salicylic acid, 5-n-octanoyl-salicylic acid) and retinoids (in particular all-trans or 13-cis retinoic acid, retinol). Unfortunately, if these active agents are used in amounts that are too great, they may cause a skin irritation. The use of these compounds, in particular for users with an irritable and/or allergic skin and/or an irritable and/or allergic scalp, should therefore be limited.

In addition, even certain compounds which are considered to be inert in a cosmetic or dermatological composition, such as, for example, preserving agents, surfactants, fragrances, solvents or propellants, may be irritant in nature when they are applied to keratin materials, and in particular the skin, including the scalp, in individuals with irritable and/or allergic skin, this irritant nature depending on the compound used and on the sensitivity of the skin and of the resident skin flora of the user.

The compounds capable of causing a skin irritation are generally used in low doses. The use of these compounds in a small amount may then prove to be relatively non-advantageous compared with the use of other compounds which are less active, but less irritant or not irritant at all, and which are therefore used in larger amount, or in relation to the purpose of the compound, for instance the stability of the composition in the case of emulsions, or good conservation of the composition in the case of preserving agents.

There exists therefore a need to find compounds with a calmative effect, capable in particular of preventing and/or reducing the irritant effect of cosmetic or dermatological compositions containing one or more compounds capable of causing a skin irritation, and of preventing and/or treating skin disorders related to a skin irritation of inflammatory or immunoallergic type.

A subject of the invention is thus also the use of at least one conditioned medium or extracts thereof, for the preparation of a composition, and the use of the composition, wherein said conditioned medium or extracts thereof is for use in preventing and/or reducing the irritant effect of a composition such as a cosmetic or dermatological composition containing one or more compounds capable of causing a skin irritation.

Whether for cosmetic or therapeutic purposes, the use according to the present invention is in particular for the treatment of irritable and/or allergic skin and/or mucous membranes and/or scalps.

A subject of the invention is also a composition for topical application to the skin and/or the mucous membranes and/or the scalp, comprising, in a physiologically acceptable medium:

at least one cosmetic or pharmaceutical compound capable of causing skin irritation, and at least one conditioned medium or extracts thereof.

The use of at least one conditioned medium, or extracts thereof, therefore has, inter alia, the advantage of eliminating the skin irritation that the compounds with an irritant side effect could have caused, and also of making it possible to increase the amount of said compounds in cosmetic or dermatological compositions compared with the amount normally used, with a view to an increased effectiveness of the latter.

Thus, it is possible to use, including in compositions for irritable and/or allergic skin and/or mucous membranes and/or scalps, agents capable of causing a skin irritation, such as cosmetic active agents (for example: keratolytic and/or desquamating agents), dermatological active agents (for example: retinoids), certain surfactants, preserving agents, fragrances, solvents and propellants, and mixtures thereof, provided that said compositions comprise at least one conditioned medium or extracts thereof.

The expression "irritable and/or allergic skin and/or mucous membranes and/or scalps" according to the invention is intended in particular to mean skin and/or mucous membranes and/or scalps which react to outside attacks, often in an exaggerated fashion. This skin and/or these mucous membranes and/or these scalps are consequently further subjected to the development of a skin reaction that can manifest itself through redness or pruritus and/or involve immunological or inflammatory mechanisms, as opposed to sensitive skin.

In the present description, unless otherwise specified, the term "skin" is intended to mean the entire covering of the human body, i.e. the skin, the mucous membranes and the scalp.

The term "integuments" is intended to mean the nails, the hair and the body hairs, such as the eyelashes.

The amount of conditioned culture medium or of extracts thereof according to the invention in the compositions will be adjusted by those skilled in the art in order to obtain the desired effect. The effective amount will thus be determined by routine techniques, comprising in vitro tests and in vivo assays, and will depend in particular on the type of extract used and on the type of formulation selected.

By way of indication, the concentration of conditioned medium active material may be between 0.001% and 50% by weight relative to the total weight of the composition, in particular less than or equal to 10%, but these amounts may vary without any drawback.

The compositions according to the invention also contain a physiologically acceptable medium, in particular a cosmetically or pharmaceutically acceptable medium. They are more particularly cosmetic or pharmaceutical compositions, in particular dermatological compositions.

For the purpose of the present invention, the term "cosmetic composition or product" is intended to mean in particular any substance or preparation intended to be brought into contact with the various superficial parts of the human body (epidermis, head hair and body hair system, nails, lips and external genital organs) or with the teeth or the oral mucous membranes, with a view, exclusively or mainly, to cleaning them, fragrancing them, modifying the appearance thereof and/or correcting body odours and/or protecting them or maintaining them in good condition (Cosmetic Guideline 76/768/EEC amended).

These compositions generally have an odour and an appearance that makes them pleasant to apply to the human body.

Preferably, a composition of the invention is applied to the skin or the mucous membranes.

According to the method of administration under consideration, it may be in any of the galenical forms normally used.

For topical application to the skin or the mucous membranes, the composition may be in the form in particular of aqueous or oily solutions or dispersions of the lotion or serum type, emulsions with a liquid or semi-liquid consistency of the milk type, obtained by dispersion of a fatty phase in an aqueous phase (O/W) or vice versa (W/O), or suspensions or emulsions with a soft consistency of the aqueous or anhydrous cream or gel type, or else microcapsules or microparticles, or vesicular dispersions of ionic and/or non-ionic type, or foams. They may also be in the form of microspheres or nanospheres or of lipid or polymeric vesicles or of polymeric patches and of hydrogels for controlled release.

According to an advantageous embodiment, the composition is a dermocosmetic composition containing, in a cosmetically or pharmaceutically acceptable support, at least one conditioned medium or one extract according to the invention, in a proportion of at least 0.001% by weight relative to the total weight of the composition, and preferably from 0.05% to 3%.

These compositions are prepared according to the usual methods.

The amounts of the various constituents of the compositions according to the invention can readily be determined by those of skill in this art in view of this disclosure and include those amounts used in the fields under consideration. The constituents and the amounts thereof will preferably be chosen so as not to interact with the activity of the conditioned medium, or of extracts thereof, by decreasing said activity.

In the cosmetics field, these compositions constitute in particular cleansing, protection, treatment or care creams for the face, for the hands, for the feet, for the large anatomical folds or for the body (for example, day creams, night creams, makeup-removing creams, foundation creams, anti-sun creams), fluid foundations, makeup-removing milks, body protection or care milks, anti-sun milks, skincare lotions, gels or foams, such as cleansing lotions, artificial-tanning lotions, bath compositions, deodorant compositions comprising a bactericidal agent, or aftershave gels or lotions.

The compositions according to the invention may also consist of solid preparations constituting soaps or cleansing bars.

The compositions may also be packaged in the form of an aerosol composition, also comprising a pressurized propellant.

A composition according to the invention may also be a scalp care composition, in particular a shampoo, a hairsetting lotion, a treating lotion, a styling gel or cream, restructing lotions for the hair, a lotion or a gel for combating hair loss, an antiparasitic shampoo, antidandruff shampoo, etc.

A composition may also be for orodental use, for example a toothpaste. In this case, the composition may contain normal adjuvants and additives for compositions for oral use, and in particular surfactants, thickeners, humectants, polishing agents such as silica, various active ingredients such as fluorides, in particular sodium fluoride, and optionally sweeteners such as sodium saccharinate.

When the composition is an emulsion, the proportion of the fatty phase may vary from approximately 5% to 80% by weight, and preferably from approximately 5% to 50% by weight, relative to the total weight of the composition. The oils, the waxes, the emulsifiers and the coemulsifiers used in the composition in emulsion form are chosen from those conventionally used in the cosmetics field. The emulsifier and the coemulsifier are present, in the composition, in a proportion ranging from 0.3% to 30% by weight, and preferably from 0.5% to 20% by weight, relative to the total weight of the composition. The emulsion may also contain lipid vesicles.

When the composition is an oily solution or gel, the fatty phase may represent more than 90% of the total weight of the composition.

In a known manner, the cosmetic composition may also contain adjuvants common in the cosmetics field, such as hydrophilic or lipophilic gelling agents, hydrophilic or lipophilic additives, preserving agents, antioxidants, solvents, fragrances, fillers, screens, odour absorbers and dyestuffs. The amounts of these various adjuvants are those conventionally used in the cosmetics field, and, for example, range from approximately 0.01% to 10% of the total weight of the composition. Depending on their nature, these adjuvants may be introduced into the fatty phase, into the aqueous phase and/or into the lipid spherules.

As oils or waxes that can be used in the invention, mention may be made of mineral oils (liquid petroleum jelly), vegetable oils (liquid fraction of shea butter, sunflower oil), animal oils (perhydrosqualene), synthetic oils (purcellin oil), silicone oils or waxes (cyclomethicone) and fluoro oils (perfluoropolyethers), beeswax, carnauba wax or paraffin wax. Fatty alcohols and fatty acids (stearic acid) may be added to these oils. As emulsifiers that can be used in the invention, mention may, for example, be made of glyceryl stearate, polysorbate 60 and the mixture of PEG-6/PEG-32/glycol stearate sold under the name Tefose® 63 by the company Gattefosse.

As solvents that can be used in the invention, mention may be made of lower alcohols, in particular ethanol and isopropanol, and propylene glycol.

As hydrophilic gelling agents that can be used in the invention, mention may be made of carboxyvinyl polymers (Carbomer®), acrylic copolymers such as acrylate/alkyl acrylate copolymers, polyacrylamides, polysaccharides such as hydroxypropylcellulose, natural gums and clays, and, as lipophilic gelling agents, mention may be made of modified clays such as bentones, metal salts of fatty acids such as aluminium stearates, hydrophobic silica, ethylcellulose and polyethylene.

The non-therapeutic use according to the present invention is in particular for preventing and/or reducing the irritant effect of a cosmetic or dermatological composition containing one or more compounds capable of causing a skin irritation.

A composition according to the present invention comprises at least one cosmetic or pharmaceutical compound capable of causing a skin irritation.

Among these compounds, mention may in particular be made of cosmetic compounds or active agents, dermatological compounds or active agents, surfactants, in particular anionic surfactants, preserving agents, detergents, fragrances, and in particular fragrancing alcoholic solutions, solvents and propellants, and mixtures thereof.

More particularly, by way of dermatological or cosmetic active agents, mention may be made of certain desquamating agents which may also be peeling agents.

Among the agents specifically for peeling, mention may be made of abrasive/exfoliating particles of mineral, organic, natural or synthetic sources. Mention may more particularly be made of pumice stone particles, silica particles, polyethylene beads, nylon beads and fruit kernel powders.

Among these desquamating agents, the following are capable of causing a skin irritation: saturated monocarboxylic acids (acetic acid) and unsaturated monocarboxylic acids, saturated and unsaturated dicarboxylic acids, saturated and unsaturated tricarboxylic acids; α-hydroxy acids and β-hydroxy acids of monocarboxylic acids; α-hydroxy acids and β-hydroxy acids of dicarboxylic acids; α-hydroxy acids and β-hydroxy acids of tricarboxylic acids, keto acids, α-keto acids or β-keto acids of polycarboxylic acids, of polyhydroxy monocarboxylic acids, of polyhydroxy dicarboxylic acids and of polyhydroxy tricarboxylic acids.

Among the α-hydroxy acids or esters thereof, mention may particularly be made of: glycolic acid, dioic acids, for instance octadecenedioic acid or Arlatone dioc DCA sold by the company Uniqema, citric acid, lactic acid, tartaric acid, maleic acid or mandelic acid, and esters thereof, such as dialkyl (C12/C13) tartrate or Cosmacol ETI, and branched C12-13 trialcohol citrate or Cosmacol ECI sold by the company Sasol.

Among the β-hydroxy acids, mention may be made of: salicylic acid and derivatives thereof (including 5-n-octanoyl-salicylic acid).

Among the α-keto acids, mention may be made of ascorbic acid and derivatives thereof.

Among the other desquamating agents, mention may be made of: pyruvic acid, gluconic acid, glucuronic acid, oxalic acid, malonic acid, succinic acid, acetic acid, gentisic acid, cinnamic acid, azelaic acid; phenol; resorcinol, urea and derivatives thereof, hydroxyethyl urea or Hydrovance® from National Starch; oligofucoses; jasmonic acid and derivatives thereof; ascorbic acid and derivatives thereof, trichloroacetic acid; extract of *Saphora japonica* and resveratrol.

Among the desquamating agents, those capable of acting on the enzymes involved in desquamation or corneodesmosome degradation may also be capable of causing a skin irritation.

Among these, mention may in particular be made of mineral salt chelating agents such as EDTA; N-acyl-N,N',N'-ethylenediaminetriacetic acid; aminosulphonic compounds, and in particular (N-2-hydroxyethyl-piperazine-N-2-ethane) sulphonic acid (HEPES); derivatives of 2-oxothiazolidine-4-carboxylic acid (procysteine); derivatives of α-amino acids of glycine type (as described in EP 0 852 949, and also sodium methyl glycine diacetate sold by BASF under the trade name Trilon M®); honey; and sugar derivatives such as O-octanoyl-6-D-maltose, O-linoleyl-6-D-glucose and N-acetyl-glucosamine.

Retinoids are also compounds capable of causing a skin irritation. Examples thereof that may be mentioned include retinol and esters thereof, retinal, retinoic acid and derivatives thereof such as those described in documents FR-A-2 570 377, EP-A-199 636, EP-A-325 540 and EP-A-402 072, and adapalene.

The salts and derivatives, such as the cis or trans forms, the racemic mixtures and the dextrorotatory or levorotatory forms of the compounds mentioned above are also considered to be compounds capable of causing a skin irritation.

Other dermatological or cosmetic active agents capable of causing a skin irritation are also mentioned below:
urea and derivatives thereof, such as hydroxyethylurea or Hydrovance® from National Starch,
certain vitamins such as vitamin D and derivatives thereof such as vitamin D3 or vitamin D2, calcitriol, calcipotriol, tacalcitol, 24,25-diOH vitamin D3, 1-OH vitamin D2 and 1,24-diOH vitamin D2; vitamin B9 and derivatives thereof,
peroxides such as benzoyl peroxide or aqueous hydrogen peroxide,
agents for combating hair loss, such as minoxidil and derivatives thereof such as aminexil,
hair dyes and hair colorants, such as aminophenols and derivatives thereof such as para-phenylenediamine (p-PDA), N-phenyl p-PDA, 2,5-toluenediamine sulphate, meta-phenylenediamine (m-PDA), 3,4-toluenediamine and ortho-phenylenediamine (o-PDA),
antiperspirants, for instance aluminium salts such as aluminium hydroxychloride,
deodorants,
hair-removing and/or permanent-waving active agents such as thioglycolates or aqueous ammonia,
thioglycolate and salts thereof,
phenoxyethanol,
1,2-pentanediol,
fragrancing alcoholic solutions (fragrances, eaux de toilette, aftershaves or deodorants),
anthralins (dioxyanthranol),
anthranoids (for example, those described in document EP-A-319028),
lithium salts,
depigmenting agents (for example: hydroquinone, vitamin C at high concentration, kojic acid),
certain slimming active agents with a heating effect,
nicotinates and derivatives thereof,
capsaicin,
anti-louse active agents (pyrethrin),
antiproliferative agents such as 5-fluorouracil or methotrexate,
antiviral agents,
antiparasitic agents,
antifungal agents,
antipruriginous agents,
antiseborrheic agents,
propigmenting agents such as psoralenes and methylangecilines, and
mixtures thereof.

As preserving agents, mention may be made of phenoxyethanol, chlorhexidine and benzalkonium chloride.

As surfactants, mention may be made of anionic, cationic and amphoteric surfactants, more particularly anionic surfactants such as alkyl sulphates and alkyl ether sulphates, for instance lauryl sulphate and lauryl ether sulphate, and in particular the sodium salts thereof.

According to a preferred embodiment of the invention, the compound capable of causing a skin irritation is chosen from retinoids, α-hydroxy acids, β-hydroxy acids, saturated and unsaturated dicarboxylic acids such as octadecenedioic acid or Arlatone DIOC DCA sold by the company Uniqema, anionic, cationic or amphoteric surfactants, 5-n-octanoylsalicylic acid, antiperspirant active agents such as aluminium salts, (N-2-hydroxyethylpiperazine-N-2-ethane)sulphonic acid (HEPES) and cinnamic acid.

The compound(s) capable of causing a skin irritation may be present in the composition according to the present invention in an amount sufficient to cause a skin irritation reaction. By way of example, it may be present at a content ranging from 0.0001% to 70% by weight, preferably from 0.01% to 50% by weight, and better still from 0.1% to 30% by weight, relative to the total weight of the composition.

In the dermocosmetic compositions according to the invention, the conditioned medium extract may be combined with retinoids or corticosteroids, or associated with free-radical scavengers, with α-hydroxy acids or α-keto acids or derivatives thereof, or else ion channel blockers.

The dermocosmetic compositions according to the invention may also contain inert or even pharmacodynamically or cosmetically active additives or combinations of these additives, and in particular: wetting agents, depigmenting agents such as hydroquinone, azelaic acid, cafeic acid or kojic acid; emollients; moisturizers such as glycerol, PEG-400 or urea; anti-ageing agents, antiseborrheic agents or anti-acne agents, such as S-carboxymethylcysteine, S-benzylcysteamine, salts thereof and derivatives thereof, or benzoyl peroxide; antibiotics such as erythromycin and esters thereof, neomycin, clindamycin and esters thereof, tetracyclines; antifungal agents such as ketoconazole or 4,5-polymethylene-3-isothiazolinones; agents for promoting hair regrowth, such as minoxidil (2,4-diamino-6-piperidinopyrimidine 3-oxide) and derivatives thereof, diazoxide (7-chloro-3-methyl-1,2,4-benzothiadiazine 1,1-dioxide) and phenyloin (5,4-diphenylimidazoline-2,4-dione); nonsteroidal anti-inflammatory agents, carotenoids, and in particular β-carotene; antipsoriatic agents such as anthraline and derivatives thereof, and, finally, eicosa-5,8,11,14-tetraenoic acid and eicosa-5,8,11-trynoic acid, esters thereof and amides.

The conditioned medium or extracts thereof, used according to the invention, may also be combined with at least 0.00001% to 95% by weight of an anti-inflammatory agent, another calmative, or a mixture thereof.

As examples of "anti-inflammatory agents", mention may be made of:
an antagonist of inflammatory cytokines;
a steroidal anti-inflammatory (hydrocortisone, betamethasone, dexamethasone, etc.);
a nonsteroidal anti-inflammatory such as aspirin; and mixtures thereof.

The anti-inflammatory agents are preferably present in the compositions in accordance with the invention at a concentration that may range approximately between 0.00001% and 10% by weight relative to the total weight of the composition. Even more preferably, the composition of anti-inflammatory compound may range between 0.0005% and 2% by weight relative to the total weight of the composition.

In particular, the other calmative may advantageously be chosen from allantoin, beta-glycyrrhetinic acid, extracts containing same, such as, for example, extract of Glycyrrhiza glabra (liquorice), and complexes containing same, such as the allantoin/glycyrrhetinic acid complex; lyophilized or non-lyophilized planktons, extracts thereof and complexes thereof; waters and extracts of flowers and of plants: chamomile water, lime water, rosewater, extracts of birch; bisabolol; essential oils, for example coriander oil; algae, in particular of the Laminaria type (for example red or brown algae), such as the extract of brown alga *Padina pavonica*, for instance HPS 3 *Padina Pavonica* sold by the company Alban Muller; acexamic acid and transexamic acid (4-trans-aminomethylcyclohexanecarboxylic acid); ursolic acid and extracts containing it, for instance extract or rosemary leaf; polysaccharides containing fucose, such as Fucogel 1000 sold by the company Solabia; electrolytes, and in particular an aqueous mixture such as "Dead Sea bath salts"; amino acids, such as Sepicalm S and VG from Seppic, and divalent magnesium salts such as magnesium gluconate.

The compositions according to the invention, in particular cosmetic or dermatological compositions, may in particular be prepared by a method comprising a first phase during which a conditioned culture medium, optionally an extract of such a conditioned culture medium, is prepared.

This method comprises at least the following steps:
a) culturing cells derived from the intestinal epithelium on a support in a first nutritive medium for a period of time sufficient to obtain their differentiation;
b) preparing a second cell culture medium in a chamber covered with peripheral blood cells or derivatives thereof, such as leukocytes,
c) recovering the culture of differentiated cells on the support, in particular a porous support, obtained at the end of step a), and transferring to the second culture medium obtained at the end of step b);
d) bringing said culture of differentiated cells derived from the intestinal epithelium, in the second culture medium, into contact with a culture of microorganisms comprising at least probiotics, which may, for example, be of the *Lactobacillus* species, for a period of time sufficient for there to be an interaction between the cells;
e) eliminating the cell cultures and recovering the second cell culture medium, freed of the leukocytes, so as to obtain a conditioned medium;
f) incorporating the conditioned medium, or an extract thereof, into a cosmetic or dermatological composition.

Preferably, the support in step a) is a porous support. The term "porous support" is intended to mean in particular an insert whose base comprises pores.

For example, the pore size may range from 0.001 to 10 μm, preferably greater than or equal to 0.3 μm. By way of non-limiting example, the base of the porous insert that is suitable for the invention may thus comprise a porous collagen matrix optionally comprising glycosaminoglycans and/or fibroblasts, a hyaluronic acid and/or collagen and/or fibronectin and/or fibrin gel or membrane, a semi-permeable nitrocellulose, nylon, Teflon, polycarbonate, polyethylene, polypropylene or polyethylene terephthalate (PET) membrane, a semi-permeable Anopore® inorganic membrane, a cellulose acetate membrane, a Biopore-CM® semi-permeable membrane, a semi-permeable polyester membrane and a polyglycolic acid membrane.

The contact time in step a) is not limited and will be adjusted by those skilled in the art, but will generally be between a few hours and a few days, in particular between 1 day and 35 days, for example from 18 to 22 days, preferably approximately 21 days. The cells which are initially arranged in a single layer thus form, at the end of step a), a three-dimensional system with several layers of differentiated cells. Advantageously, the culture medium will be renewed regularly, for example every 2 days, so as to obtain optimal differentiation of the cells derived from the intestinal epithelium, such as Caco2 cells.

In step b), the peripheral blood cells or derivatives thereof, in particular the leukocytes form a carpet of cells; i.e. the surface of the chamber is substantially homogeneously covered with leukocytes; the latter may be in the form of a monolayer or in multilayers.

These leukocytes will in particular be collected from a blood sample after at least one separation step, in particular by centrifugation, and then at least partial elimination of the monocytes. They are then resuspended in a nutritive medium compatible with their viability, in particular RPMI medium.

In general, the media may be chosen by those skilled in the art according to their general knowledge, and in particular from the media mentioned above.

By way of example of a chamber suitable for implementing the invention, mention may be made of the wells of culture plates such as 6-, 12-, 24-, 48-well or 96-well cell culture plates commonly used in cell culture.

Advantageously, the differentiated cell culture will be washed with the medium suitable for the viability of the leukocytes before the transfer in step c). The contacting between the differentiated cells and the probiotics, in the presence of the leukocytes, will be carried out for a period of time that allows interactions to be established, i.e. chemical or biological exchanges between the various cell types.

For the purpose of the invention, the expression "cellular chemical exchange" is intended to denote all the signals represented by molecules, released from a cell, and capable of affecting, remotely, the activity of another cell which may or may not belong to the same cell type. Such a molecule may, for example, and in a nonlimiting manner, be a peptide, a protein, a lipid, a sugar, a steroid hormone or a catecholamine. It may be released in the form of a secretion.

It is understood that this interaction can occur in the absence of direct physical contact between the various cell types; in particular, the arrangement by which, firstly, the cells derived from the intestinal epithelium and, secondly, the cell carpet of leukocytes, which may or may not be placed in a single chamber, are brought into communication with one another by means of the culture medium in which they are incubated, without cells of the intestinal cell culture being able to enter directly into contact with cells of another cell carpet, for example by contact between the cell bodies or by means of cell extensions. Advantageously, the probiotic microorganisms are added to the intestinal cell culture apically.

The period of time suitable for the establishment of this interaction will be a few hours to several days, generally at least 6 hours, preferably at least 10, in particular greater than or equal to 16 hours, but may be extended without any drawback. The probiotics are, for example, left in contact with the intestinal cells in the chamber comprising the leukocytes for 6 to 36 hours.

The culture medium is then recovered by separating it from all the cells, for example by harvesting it at the basolateral level: this conditioned medium has been influenced by the two cell types and their interrelationship.

As indicated before, the culture medium such recovered, also called "conditioned medium" contains IL-10 in a concentration greater or equal to 20 pg/ml, in particular from 50 to 200 pg/ml.

It may subsequently be subjected to concentration, extraction and/or fractionation steps known per se to those skilled in the art, before the introduction, as an ingredient, into a composition, in particular a cosmetic or pharmaceutical or dermocosmetic composition according to the invention.

The invention will be illustrated in greater detail in the examples which follow.

EXAMPLE 1

Preparation of a Conditioned Medium

Cells close to human enterocytes, Caco2 (between passage 60 and 65) are seeded at the density of $2.5 \times 10^5$ cells/ml in a 25 mm culture insert (having nucleopores of 0.4 μm, Becton Dickinson, Basle, Switzerland). These inserts are placed in a culture dish (Nunc) and cultured for 18 to 22 days at 37° C./10% $CO_2$ in DMEM (containing glutamine and a high concentration of glucose (Amimed, Allschwill, Switzerland)) supplemented with nonessential amino acids (Gibco, BRL), 10 mg/ml gentamycin (GIBCO BRL) and 0.1% of penicillin/streptomycin (10 000 IU/ml and 10 000 μg/ml) (GIBCO). The culture medium is changed every 2 days until the cells are completely differentiated (21 days). A measurement of transepithelial electrical resistance is continually determined when the Caco2 cells are confluent in a monolayer, using a multicell-ERS electrode (volt meter/ohm meter).

Moreover, blood leukocytes from normal volunteers are isolated from peripheral blood of unrelated normal donors, by centrifugation on Lymphoprep. The cell suspensions ($10^7$ cells/ml) are placed in a petri dish and incubation for 1 h 30 at 37° C. allows the monocytes to adhere. Thus, the leukocytes, predominantly T lymphocytes, contained in the population of nonadherent cells, are purified using their property of forming rosettes in the presence of sheep red blood cells. The latter are then eliminated by osmotic shock in the presence of $NH_4Cl$ (8.7 mg/l). In all cases, the viability of the leukocyte suspension is greater than 95%.

These leukocytes are then diluted in RPMI 1640 containing 20% of decomplemented human AB serum (decomplementation at 56° C. for 30 minutes, Sigma, St Louis, Mo., USA).

The Caco2/leukocyte coculture model can then be prepared. For this, the Caco2 cell culture inserts are washed twice in RPMI 1640 medium and transferred into a 6-well culture plate containing RPMI medium, in which the wells have been previously coated with a carpet of freshly purified leukocytes ($2 \times 10^6$ cells/ml). Thus, the leukocytes are at the basolateral level and the Caco2 cells are at the apical level.

The stimulation of the Caco2/leukocyte (peripheral blood white blood cells) cocultures with probiotics is carried out according to the conditions described below:

Thus, $1 \times 10^7$ cfu/ml of probiotics are added apically. The culture medium alone is used as negative control. After stimulation for 6 to 36 h (37° C., 10% $CO_2$), of the coculture, the conditioned medium is harvested basolaterally.

Lactobacillus paracasei, in particular the strain deposited with the CNCM under No. CNCM I-2116, is in particular used as probiotic.

EXAMPLE 2

An intestinal cell line Caco2 is cultured on 10.5 mm inserts (Becton Dickinson) at a rate of $2 \times 10^5$ cells/well. These inserts are then placed in culture in a 12-well plate (Nunc). The cells are then cultured for 21 days at 37° C./10% $CO_2$ in DMEM supplemented with 10% FCS and 0.1% of penicillin/streptomycin (10 000 IU/ml, Gibco BRL).

Human peripheral blood mononuclear cells (leukocytes) are purified from blood bag buffy coats by centrifugation through a Ficoll-Hypaque 1077 column (Pharmacia) and are then resuspended in complete RPMI medium supplemented with human AB serum (Gibco BRL). The leukocytes ($2 \times 10^6$ cells/ml) are then added to the basolateral compartment of the "trans-well" cultures when the latter exhibit a confluent layer of Caco2 cells, which have been previously washed with their medium.

The cocultures thus established are stimulated by adding $1 \times 10^7$ cfu/ml of probiotics to the apical surface of the monolayer of epithelial cells (Caco2). The system is then incubated for 16 h at 37° C./5% $CO_2$. 150 μg/ml of gentamycin are added to the medium after 4 h of incubation.

At the end of incubation (16 h), the medium that is in the basolateral compartment is removed to be tested.

The following table illustrates the cytokine profile of conditioned media derived from the stimulation with $1 \times 10^7$ cfu/ml of *Lactobacillus paracasei* and of *Bifidobacterium longum* for 16 h.

|  | IL 10 pg/ml | IFN gamma pg/ml |
|---|---|---|
| B. longum | 170 | 110 |
| L. paracasei | 80 | 40 |
| B. longum + L. paracasei | 110 | 40 |

These results show that the probiotics preferentially induce the production of the regulatory cytokine IL-10 rather than the pro-inflammatory cytokine IFN-γ.

EXAMPLE 3

Evaluation of the Inhibition of Inflammation in a Human Skin Model Under Survival Conditions Conditioned medium is prepared according to the protocol of Example 1, using $1 \times 10^7$ cfu/ml of *Lactobacillus paracasei*.

A human skin model maintained under survival conditions, stimulated with a neuromediator (substance P, SP), was used. This neuromediator is in fact one of the agents responsible for the inflammatory response. Along with its vascular effects (oedema, vasodilation, expression of ELAM-1 on the endothelial cell wall), SP, under the conditions of the test, also induces biochemical reactions with release of pro-inflammatory mediators (1L1α, IL6, TNFα) and also mast cell degranulation (Lembeck F., 1983; Matsuda H. et al., 1989; Weidner C. et al., 2000).

The evaluation was carried out histologically (evaluation of oedema, modifications of capillary diameter and of the number of degranulated mast cells) and biochemically (assaying of TNFα).

Fragments of skin from different donors were placed in inserts that were themselves arranged in suspension above culture wells. Medium (Dulbecco's minimum essential medium, DMEM) (antibiotics, FCS) was added to the bottom of the wells, passage occurring by slow diffusion between the two compartments via a porous membrane (0.45 μm). Five hours of re-equilibration are necessary before beginning the protocol.

After the 5 hours of re-equilibration, the conditioned media stimulated (or not) with *L. paracasei* were added as pretreatment to the DMEM culture medium at the concentration of 30%. The skin fragments were then maintained in organ culture for 24 hours in an incubator under a humid atmosphere, at 37° C. and in the presence of 5% $CO_2$.

At D1, the experimental inflammation model was prepared by adding 10 μM of substance P to the culture medium. The nutritive media were renewed and a further 24 hours of incubation were carried out for all the conditions.

A comparative study was thus carried out between the following 8 conditions:

SP Stimulation Model in Comparison with Control Skin:
  control skin (basic condition: skin not stimulated, not treated) with DMEM medium,
  skin stimulated with 5 μM substance P in DMEM medium,
Absolute Control (Condition A):
  skin cultured with nutritive medium (RPMI) at 30% in DMEM medium,
  skin stimulated with substance P and cultured with nutritive medium (RPMI) at 30% in the DMEM medium,
Negative Control (Condition B):
  skin cultured with nutritive medium (RPMI) at 30% derived from a Caco2/PBMC coculture, not stimulated with lactic ferments,
  skin stimulated with substance P and cultured with the conditioned medium, not stimulated with *Lactobacillus paracasei*,
Positive Control (Condition C):
  skin cultured with nutritive medium (RPMI) at 30% derived from a Caco2/PBMC coculture, stimulated with *Lactobacillus paracasei*,
  skin stimulated with substance P and cultured with the conditioned medium, stimulated with *L. paracasei*.

1—Histological Evaluation of the Oedema and of the Modifications of Capillary Diameter The skin fragments were fixed in Bouin's solution and paraffin-embedded. After staining with hemalun-eosin, 2 criteria were evaluated at the dermal level: capillary calibre and oedema.

The results are the following:
a) Evaluation of the Overall % of Dilated Capillaries
  SP stimulation model in comparison with the control skin:
  The application of SP induces statistically significant vasodilation compared with the control skin: 84.5% versus 58.3% ($p<0.05$).
Absolute Control (Condition A):
  As in the experimental model, statistically significant dilation of the capillaries was observed after application of substance P: 78.3% versus 61.5% ($p<0.05$).
Negative Control (Condition B):
  The results are similar to those obtained with condition A, statistically significant dilation of the capillaries is observed after application of substance P, attesting to the absence of an anti-inflammatory effect of the non-stimulated conditioned medium: 82.2% versus 56.7% ($p<0.05$).
Positive Control (Condition C):
  No modification of the % of dilated capillaries between the conditions C and C+SP (60.9% versus 54.9%), attesting to the anti-inflammatory effect of the conditioned medium stimulated with *Lactobacillus paracasei*. This result is confirmed by the existence of a statistically significant difference between the condition C+SP and the other conditions: control+SP, A+SP and B+SP ($p<0.05$).

b) Measurement of the Average Surface of the Capillaries
  The results concerning the measurement of the average surface of the capillaries are similar to those obtained with the analysis of the overall % of dilated capillaries.
  SP stimulation model in comparison with control skin:
  The application of SP induces statistically significant vasodilation compared with the control skin: 164.5 $\mu m^2$ versus 69 $\mu m^2$ ($p<0.05$).
Absolute Control (Condition A):
  As in the experimental model, we observe statistically significant dilation of the capillaries after application of substance P: 127.8 $\mu m^2$ versus 57 $\mu m^2$ ($p<0.05$).
Negative Control (Condition B):
  The results are similar to those obtained with condition A, statistically significant dilation of the capillaries is observed after application of substance P, attesting to the absence of an anti-inflammatory effect of the non-stimulated conditioned medium: 154 $\mu m^2$ versus 67 $\mu m^2$ ($p<0.05$).
Positive Control (Condition C):
  A significant decrease in the surface of the dilated capillaries for the condition C+SP compared with the condition C (59.2 $\mu m^2$ versus 87 $\mu m^2$), attesting to the anti-inflammatory effect of the conditioned medium stimulated with *L. paracasei* ($p<0.05$). This result is confirmed by the existence of a statistically significant difference between the condition C+SP and the other conditions: control+SP, A+SP and B+SP ($p<0.05$).

Evaluation of the Dermal Oedema
  SP stimulation model in comparison with control skin:
  The application of SP induces a statistically significant oedema compared with the control skin: score of 1.8 versus 0.7 ($p<0.05$).
Absolute Control (Condition A):
  As in the experimental model, we observe statistically significant oedema after application of substance P: score of 1.9 versus 1.3 ($p<0.05$).
Negative Control (Condition B):
  The results are similar to those obtained with condition A, an oedema was noted after application of substance P, attesting to the absence of an anti-inflammatory effect of the non-stimulated conditioned medium: score of 1.9 versus 0.8 ($p<0.05$).
Positive Control (Condition C):
  No increase in the oedema in the condition C+SP compared with condition C (0.9 versus 1) was obtained, attesting to the anti-inflammatory effect of the conditioned medium stimulated with *L. paracasei*. This result is confirmed by the existence of a statistically significant difference between the condition C+SP and the other conditions: control+SP, A+SP and B+SP ($p<0.05$).

2—Histological Evaluation of the Mast Cell Degranulation

The mast cells present in the dermis were revealed in blue-purple by staining with toluidine blue. Histologically, a more or less intense blue-purple and granular appearance of the mast cells in relation to the more or less substantial presence, in their cytoplasm, of basophilic and metachromatic granulations containing in particular histamine was observed.

In the SP-stimulated model of skin maintained under survival conditions, a statistically significant decrease in the % of highly granulated mast cells (score 3) was observed: 32.1% versus 53% in terms of the control skins, and an increase in the % of cells having a score of 1 was observed: 26.5% versus 9.5%. A substance P-induced degranulation is thus indeed obtained.

Absolute Control (Condition A):

As in the experimental model, a decrease in the % of mast cells having a score of 3 is observed: 14.8% versus 41.7% and an increase in score 1 is observed: 36.9% versus 12.2% ($p<0.05$).

Negative Control (Condition B):

The results are similar to those obtained with condition A with a decrease in the % of mast cells having a score of 3: 17.5% versus 38.5% and an increase in the % of cells having a score 1: 33.3% versus 20.4% ($p<0.05$). These results make it possible to conclude that the non-stimulated conditioned medium does not protect against substance P-induced degranulation.

Positive Control (Condition C):

No significant difference between the % of mast cells having a score of 3 in condition C and that observed in condition C+SP was obtained (score of 46.9% versus 37.2%). This lack of difference may therefore attest to a moderate protective effect of the conditioned medium stimulated with *L. paracasei* with respect to substance P-induced degranulation. This effect is partial since the % of mast cells having a score of 1 is increased but of a lower level than in the other conditions: control+SP, A+SP and B+SP ($p<0.05$). Nevertheless, since this increase is small, we find a statistically significant difference between the condition C+SP and the other conditions: control+SP, A+SP and B+SP ($p<0.05$).

3—Assaying of Pro-Inflammatory Cytokine

The modulation of the secretion of cytokines such as TNF-α was investigated.

This cytokine was assayed by an immunoassay technique with spectrophotometric reading of the concentration (pg/ml) (assay kits Chemicon International Inc.). Since the skin fragments have the same surface area (verification of the weight of each fragment), the assay was carried out using the culture supernatants.

The results of the TNF assay are the following:

In the control skin and condition A corresponding to absolute control, the application of SP induces a statistically significant increase in the amount of TNF compared with the control skin: respectively, score of 31.5 versus 10.7 and score of 28.6 versus 8.32 pg/ml ($p<0.05$).

The condition C+SP is statistically different from the condition control skin+SP ($p=0.017$), suggesting that the *L. paracasei* conditioned medium decreases the production of TNF-α (amount of 10.9 versus 16.3 pg/ml).

Conclusion

In this model of human skin maintained under survival conditions, an anti-inflammatory effect of the conditioned medium stimulated with *L. paracasei* (C) was demonstrated, with a considerable and statistically significant decrease in vasodilation, in induced oedema, in mast cell degranulation and in the release of TNF induced by substance P, compared with the conditions A+SP (RPMI medium) and B+SP (non-stimulated conditioned medium).

EXAMPLE 4

Evaluation of the Inhibition of the Inflammation in a Model of Human Skin under Survival Conditions Conditioned medium is prepared according to the protocol of Example 1, using $1\times10^7$ cfu/ml of *Lactobacillus paracasei* or *Bifidobacterium longum*.

A model of human skin maintained under survival conditions, stimulated with a neuromediator (substance P, SP), was used. This neuromediator is in fact one of the agents responsible for the inflammatory response and the vascular effects (oedema, vasodilation, expression of ELAM-1 on the endothelial cell wall). The evaluation was carried out histologically (evaluation of oedema, modifications of capillary diameter).

Fragments of skin from different donors were placed in inserts which were themselves arranged in suspension above culture wells. Medium (Dulbecco's minimum essential medium) (DMEM) (antibiotics, FCS) was added to the bottom of the wells, passage occurring by slow diffusion between the two compartments via a porous membrane (0.45 μm). Five hours of re-equilibration are necessary before beginning the protocol.

After the 5 hours of re-equilibration, the conditioned medium stimulated (or not) with *L. paracasei* and/or *B. longum* was added as pre-treatment to the DMEM culture medium at the concentration of 30%. The skin fragments were then maintained in organ culture for 24 hours in an incubator under a humid atmosphere, at 37° C. and in the presence of 5% $CO_2$.

At D1, the experimental inflammation model was prepared by adding 10 μM of substance P to the culture medium. The nutritive media were renewed and a further 24 hours of incubation were carried out for all the conditions.

A comparative study was thus carried out between the following 8 conditions:

SP Stimulation Model in Comparison with the Control Skin:
    control skin (basic condition: skin not stimulated, not treated) with DMEM medium,
    skin stimulated with 5 μM substance P in DMEM medium, Absolute Control (Condition 1):
    skin cultured with RPMI nutritive medium at 30% in DMEM medium,
    skin stimulated with substance P and cultured with nutritive medium (RPMI) at 30% in the DMEM medium, Negative Control (Condition 2):
    skin cultured with nutritive medium (RPMI) at 30% derived from a Caco2/PBMC coculture, not stimulated with lactic ferments,
    skin stimulated with substance P and cultured with the conditioned medium, not stimulated with probiotics, Condition 3:
    skin cultured with nutritive medium (RPMI) at 30% derived from a Caco2/PBMC coculture, stimulated with *Lactobacillus paracasei+Bifidobacterium longum,*
    skin stimulated with substance P and cultured with the conditioned medium, stimulated with *L. paracasei+B. longum,*

Condition 4:
    skin cultured with nutritive medium (RPMI) at 30% derived from a Caco2/PBMC coculture, stimulated with *Lactobacillus paracasei,*
    skin stimulated with substance P and cultured with the conditioned medium, stimulated with *L. paracasei,*

Condition 5:
    skin cultured with nutritive medium (RPMI) at 30% derived from a Caco2/PBMC coculture, stimulated with *Bifidobacterium longum,*
    skin stimulated with substance P and cultured with the conditioned medium, stimulated with *B. longum.*

Histological Evaluation of the Oedema and of the Modifications of Capillary Diameter The skin fragments were fixed in Bouin's solution and paraffin-embedded. After staining with hemalun-eosin, 2 criteria were evaluated at the dermal level: capillary calibre and oedema.

The results are the following:
a) Evaluation of the Overall % of Dilated Capillaries
Absolute Control (Condition 1):
As in the experimental model, statistically significant dilation of the capillaries was observed after application of substance P: 86.6% versus 63.8% ($p<0.05$).
Negative Control (Condition 2):
The results are similar to those obtained with condition 1, statistically significant dilation of the capillaries is observed after application of substance P, attesting to the absence of an anti-inflammatory effect of the non-stimulated conditioned medium: 86.1% versus 75.3% ($p<0.05$).
Condition 3:
No modification of the % of dilated capillaries between conditions 3 and 3+SP (72.4% versus 72.4%), attesting to the anti-inflammatory effect of the conditioned medium stimulated with *Lactobacillus paracasei+B. longum*. This result is confirmed by the existence of a statistically significant difference between condition 3+SP and the other conditions: control+SP, 1+SP and 2+SP ($p<0.05$).
Condition 4:
No modification of the % of dilated capillaries between conditions 4 and 4+SP (73.2% versus 71.6%), attesting to the anti-inflammatory effect of the conditioned medium stimulated with *Lactobacillus paracasei*. This result is confirmed by the existence of a statistically significant difference between condition 4+SP and the other conditions: control+SP, 1+SP and 2+SP ($p<0.05$).
Condition 5:
No modification of the % of dilated capillaries between conditions 5 and 5+SP (75.6% versus 66.9%), attesting to the anti-inflammatory effect of the conditioned medium stimulated with *B. longum*. This result is confirmed by the existence of a statistically significant difference between condition 5+SP and the other conditions: control+SP, 1+SP and 2+SP ($p<0.05$).
b) Measurement of the Average Surface of the Capillaries
The results concerning the measurement of the average surface of the capillaries are similar to those obtained with the analysis of the overall % of dilated capillaries.
Absolute Control (Condition 1):
As in the experimental model, statistically significant dilation of the capillaries after application of substance P is observed: 172.6 $\mu m^2$ versus 95.36 $\mu m^2$ ($p<0.05$).
Negative Control (Condition 2):
The results are similar to those obtained with condition 1, statistically significant dilation of the capillaries is observed after application of substance P, attesting to the absence of an anti-inflammatory effect of the non-stimulated conditioned medium: 163.8 $\mu m^2$ versus 110.3 $\mu m^2$ ($p<0.05$).
Condition 3:
A significant decrease in the surface of the dilated capillaries for condition 3+SP compared with condition 3 (121.9 $\mu m^2$ versus 102 $\mu m^2$), attesting to the anti-inflammatory effect of the conditioned medium stimulated with *L. paracasei+B. longum* ($p<0.05$). This result is confirmed by the existence of a statistically significant difference between condition 3+SP and the other conditions: 1+SP and 2+SP ($p<0.05$).
Condition 4:
A significant decrease in the surface of the dilated capillaries for condition 3+SP compared with condition 4 (112.3 $\mu m^2$ versus 117.4 $\mu m^2$), attesting to the anti-inflammatory effect of the conditioned medium stimulated with *L. paracasei* ($p<0.05$). This result is confirmed by the existence of a statistically significant difference between condition 4+SP and the other conditions: 1+SP and 2+SP ($p<0.05$).

Condition 5:
A significant decrease in the surface of the dilated capillaries for condition 5+SP compared with condition 5 (110.4 $\mu m^2$ versus 105.7 $\mu m^2$), attesting to the anti-inflammatory effect of the conditioned medium stimulated with *B. longum* ($p<0.05$). This result is confirmed by the existence of a statistically significant difference between condition 5+SP and the other conditions: 1+SP and 2+SP ($p<0.05$).
Evaluation of the Dermal Oedema
Absolute Control (Condition 1):
As in the experimental model, a statistically significant oedema is observed after application of substance P: score of 1.7 versus 1.05 ($p<0.05$).
Negative Control (Condition 2):
The results are similar to those obtained with condition 1: an oedema was noted after application of substance P, attesting to the absence of an anti-inflammatory effect of the non-stimulated conditioned medium: score of 1.4 versus 1.3 ($p<0.05$).
Condition 3:
No increase in the oedema in condition 3+SP compared with condition 3 (1.23 versus 1.17) was obtained, attesting to the anti-inflammatory effect of the conditioned medium stimulated with *L. paracasei+B. longum*. This result is confirmed by the existence of a statistically significant difference between condition 3+SP and the other conditions: 1+SP and 2+SP ($p<0.05$).
Condition 4:
No increase in the oedema in condition 4+SP compared with condition 4 (1.37 versus 1.38) was obtained, attesting to the anti-inflammatory effect of the conditioned medium stimulated with *L. paracasei*. This result is confirmed by the existence of a statistically significant difference between condition 3+SP and the other conditions: 1+SP and 2+SP ($p<0.05$).
Condition 5:
No increase in the oedema in condition 5+SP compared with condition 5 (1.4 versus 1.06) was obtained, attesting to the anti-inflammatory effect of the conditioned medium stimulated with *B. longum*. This result is confirmed by the existence of a statistically significant difference between condition 3+SP and the other conditions: 1+SP and 2+SP ($p<0.05$).

EXAMPLE 5

Compositions

| Composition for preparing the skin for sunlight | |
|---|---|
| Stimulated conditioned medium* | 2.5% |
| Preserving agents | 1.35% |
| Sodium citrate | 0.035% |
| PEG-40 | 1.25% |
| Pentaerythrityl tetraethylhexanoate | 4% |
| Glycerol | 7% |
| Sorbitan tristearate | 0.3% |
| *Prunus armeniaca* kernel oil | 2% |
| Cetyl alcohol | 0.7% |
| Propylene glycol | 2% |
| Triethanolamine | 0.4% |
| Cyclohexasiloxane | 2% |
| Carbomer | 0.75% |
| Tocopherol | 1% |
| Silica | 2% |
| Ascorbyl glucoside | 0.1% |

| Composition for preparing the skin for sunlight | |
| --- | --- |
| Polycaprolactone-beta-carotene | 5% |
| Water qs | 100% |

*Obtained according to Example 1

| Composition containing sunscreens | |
| --- | --- |
| Stimulated conditioned medium** | 3.5% |
| Mixture of cetylstearyl alcohol and of oxyethylenated cetylstearyl alcohol (33 EO) 80/20 | 7.0% |
| Mixture of glyceryl monostearate and distearate | 2.0% |
| Cetyl alcohol | 1.5% |
| Polydimethylsiloxane | 1.5% |
| Liquid petroleum jelly | 15.0% |
| Butylmethoxydibenzoylmethane | 3.0% |
| Octocrylene | 7.0% |
| Glycerol | 20.0% |
| Demineralized water | qs 100% |

**Obtained according to Example 1, but with a mixture of *L. paracasei* and *B. longum*

| Cream | |
| --- | --- |
| Extract of conditioned medium* | 1.5% |
| Glyceryl stearate and PEG 100 stearate | 5.0% |
| Isohexadecane | 8.0% |
| Shea butter | 5.0% |
| Glycerol | 3.0% |
| Carbopol 981 0.2% | 0.2% |
| Lubragel | 5.0% |
| Phenoxyethanol | 1.0% |
| Citric acid | 1.0% |
| BHT | 0.05% |
| Water | qs 100% |

*Obtained according to Example 1 and lyophilized.

The above written description of the invention provides a manner and process of making and using it such that any person skilled in this art is enabled to make and use the same, this enablement being provided in particular for the subject matter of the appended claims, which make up a part of the original description and including the use of at least one conditioned cell culture medium or of an extract thereof, for the preparation of a composition for use in the treatment of the signs of inflammation and/or of immune disorders, said medium being able to be obtained by contact with at least one culture of digestive tract cells and at least probiotic microorganisms, and/or said medium being able to be obtained by contact with at least one culture of digestive tract cells and at least one probiotic microorganism.

As used herein, the phrases "selected from the group consisting of," "chosen from," and the like include mixtures of the specified materials. Terms such as "contain(s)" and the like as used herein are open terms meaning 'including at least' unless otherwise specifically noted. Phrases such as "mention may be made," etc. preface examples of materials that can be used and do not limit the invention to the specific materials, etc., listed.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A method for treating the signs of inflammation and irritation of skin and/or scalp or treating the signs of inflammatory skin and/or scalp disorders the method comprising applying an effective amount of a conditioned cell-free culture medium and/or an extract of the conditioned cell-free culture medium to the skin and/or the scalp of a person in need thereof,
wherein said medium is conditioned by contacting at least one culture of digestive tract cells, at least one culture of a probiotic microorganism, and a culture of peripheral blood cells in a culture medium and incubating under conditions suitable to condition said medium.

2. The method according to claim 1, wherein the peripheral blood cells are leukocytes.

3. The method according to claim 1, wherein the digestive cells are intestinal epithelial cells.

4. The method according to claim 1, wherein the at least one probiotic microorganism is at least one probiotic microorganism selected from the group consisting of: *Saccharomyces, Yarrowia, Kluyveromyces, Torulaspora, Schizosaccharomyces pombe, Debaromyces, Candida, Pichia, Aspergillus, Penicillium, Bifidobacterium, Bacteroides, Fusobacterium, Melissococcus, Propionibacterium, Enterococcus, Lactococcus, Staphylococcus, Peptostrepococcus, Bacillus, Pediococcus, Micrococcus, Leuconostoc, Weissella, Aerococcus, Oenococcus,* and *Lactobacillus*.

5. The method according to claim 1, wherein the at least one probiotic microorganism is selected from the group consisting of Lactic acid bacteria, Bifidobacteria, *Saccharomyces* yeasts, and mixtures thereof.

6. The method according to claim 1, wherein the at least one probiotic microorganism is selected from the group consisting of *Lactobacillus* and *Bifidobacterium* species, and mixtures thereof.

7. The method according to claim 1, wherein the conditioned cell-free culture medium and/or an extract of the conditioned cell-free culture medium is a cosmetic or pharmaceutical composition.

8. The method according to claim 1, further comprising applying at least one agent that causes skin irritation.

* * * * *